United States Patent [19]

Ågren et al.

[11] Patent Number: 4,685,907
[45] Date of Patent: Aug. 11, 1987

[54] DRESSING AND A METHOD FOR THE MANUFACTURE THEREOF

[75] Inventors: Magnus Ågren, Göteborg; Percy Nordqvist, deceased, late of Särö, both of Sweden, by Ulla Nordqvist, Per Nordqvist, Patrik Nordqvist, heirs

[73] Assignee: Molnlycke AB, Molnlycke, Sweden

[21] Appl. No.: 703,130

[22] Filed: Feb. 19, 1985

[30] Foreign Application Priority Data

Feb. 17, 1984 [SE] Sweden ................................ 8400855

[51] Int. Cl.⁴ ............................................. A61F 13/00
[52] U.S. Cl. .................................... 604/304; 604/896; 128/156
[58] Field of Search .............. 604/304, 359, 360, 365, 604/367, 368; 128/153–156

[56] References Cited

U.S. PATENT DOCUMENTS

| | | | |
|---|---|---|---|
| 2,063,218 | 12/1936 | Zisserman et al. | 424/28 |
| 3,872,862 | 3/1975 | Hume | 604/308 |
| 4,049,802 | 9/1977 | Fox, Jr. | 514/157 |
| 4,214,582 | 7/1980 | Patel | 128/156 |
| 4,307,717 | 12/1981 | Hymes et al. | 128/156 |
| 4,310,509 | 1/1982 | Berglund et al. | 128/156 |
| 4,401,651 | 8/1983 | Knutson | 514/53 |
| 4,486,488 | 12/1984 | Pietsch et al. | 128/156 |

FOREIGN PATENT DOCUMENTS

| | | |
|---|---|---|
| 1282228 | 11/1968 | Fed. Rep. of Germany . |
| 3033606 | 4/1982 | Fed. Rep. of Germany . |
| WO79/00871 | 11/1979 | World Int. Prop. O. .......... 604/304 |
| 399822 | 3/1978 | Sweden . |

Primary Examiner—C. Fred Rosenbaum
Assistant Examiner—Jerome R. Smith, Jr.
Attorney, Agent, or Firm—Young & Thompson

[57] ABSTRACT

The invention relates to a dressing which incorporates substance for cleansing sores and stimulating the healing thereof. The substance is zinc oxide, which is bound in the dressing with the aid of a tissue-compatible polymer. The invention also relates to a method for preparing such dressings.

9 Claims, 4 Drawing Figures

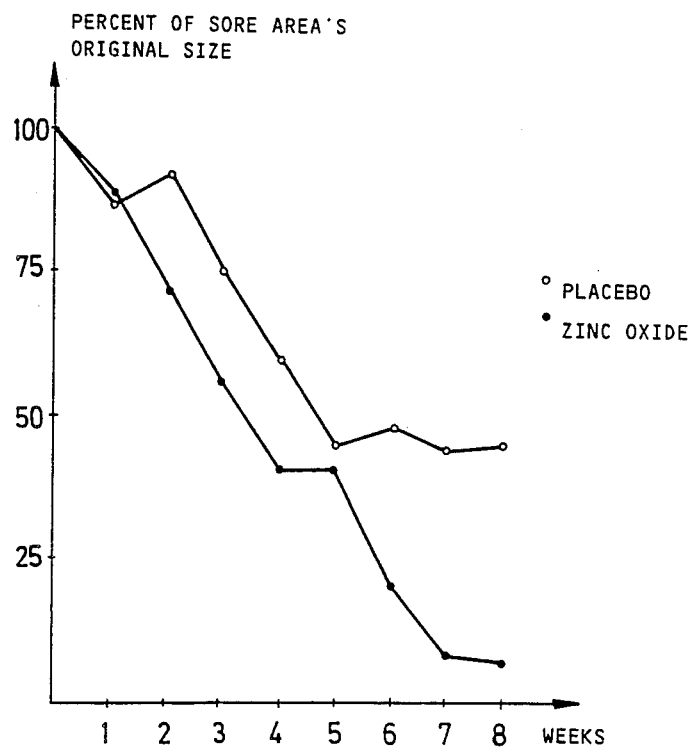

DRESSING AND A METHOD FOR THE MANUFACTURE THEREOF

The present invention relates to a medicated dressing containing substance for cleansing open sores and stimulating the healing thereof.

Various kinds of materials are known to the art with which open sores can be cleansed and dried. Normally, besmeared sores are treated with moist common salt dressings. Although such dressings are satisfactory in themselves, they are encumbered with a number of disadvantages. For example moist dressings are relatively difficult to handle. Another disadvantage with moist, common salt dressings is that the dressing should preferably be changed every six hours. Consequently, in recent times attempts have been made to use dry common salt dressings, which are easier to handle and need not be changed as often as moist dressings.

The present invention is based on the understanding that zinc oxide has a positive healing effect on open sores and like wounds.

In itself, zinc has long been used in the treatment and healing of open sores bound to an unguent or ointment base, such as paraffin or vaseline. Such ointments, however, cannot safely be applied to open sores.

In the treatment of burns, a number of attempts have been made in the past to apply zinc locally, directly to the afflicted or burned area itself. These trials were effected with the aid of zinc tape, in which zinc oxide is fixated in the tape adhesive. Such tapes have been relatively successful in treating burns, and it has been found that the zinc content in serum and at the site of the afflicted area has increased, while establishing a reduction in the zinc content of the tape at the same time.

Zinc-oxide tape dressings are also encumbered with disadvantages, however. In this form of treatment the body temperature of the patients tends to rise quite considerably, especially when the surface area the dressing is greater than 5% of the body surface, which is assumed to be due to the fact that during the initial treatment stages the dressing is too tight to allow the requisite evaporation of body fluid to take place. In addition, tape dressings are not suitable for use with all types of sores, and especially not infected sores, where the tape creates occlusions, thereby providing conditions favourable to the growth of bacteria.

Hitherto there has been no clear evidence that zinc actually has a favourable healing effect on open sores and wounds. On the other hand it is fully evident that an open sore will not heal satisfactorily if the patient has a zinc deficiency. It has been suggested that patients be given zinc sulphate orally, to improve healing of their sores. Tests have shown, however, that it takes several weeks before a therapeutic zinc level is obtained in serum. One explanation for this is that zinc is not only taken up in sore tissue, but also in other parts of the body.

According to one biochemical theory zinc has the following effect on cells and biomembranes in vivo.

1. Only the trace metals zinc and mercury stimulate lymphocyte DNA-synthesis and function in this respect as a non-specific mitogene. Lymphocytes are unavoidably necessary for immunoreactions, and it is undeniable that immunity plays an important part in the healing of open sores. In this context it is significant that serum protein must be present and that it should be maintained within the region of $15-45\times10^{-5}$M in order for the zinc concentration to have an optimal effect.

2. Zinc has an inhibiting effect on the rupturing tendencies of most cells. Among other things, histamine is released locally when mast cells rupture, which has a deleterious effect on the healing process of open sores and like wounds. According to certain hypotheses, even trophical sores are created when histamine is released locally. Zinc also has a stabilizing effect on lysosomala vacuolar membranes. The contents of these vacuoles is highly toxic to tissue. The effect of zinc on mast cell membranes does not appear particularly contingent on concentration.

3. Small thrombus often form in the region of a wound or sore and inhibit healing processes by impairing blood circulation. Thrombus are formed by the initial aggregation of thrombocytes, from which the actual thrombus breaks away. Consequently, it is extremely important to prevent the aggregation of thrombocytes. Zinc applied locally to tissue will inhibit thrombocyte aggregation at a concentration as low as $1.0-1.5\times10^{-5}$M.

According to Sections 1, 2 and 3 above, zinc has a positive healing effect on open sores, provided that the correct concentrations are observed with local application.

4. The effect of zinc on macrophages and polymorphonuclear white blood cells, i.e. those cells which control defence against infection.

High concentrations of zinc in serum greatly reduce the migration ability of microphages and almost completely stops mobility and the phagorytation ability of polymorphonuclear leucocytes. Varying zinc concentrations in the medium also affects the amount of oxygen absorbed by activated leucocytes. Tests carried out on animals have shown that the zinc concentration in serum should not exceed $3\times10^{-5}$M.

In summary it can be said that in order to achieve a positive result when treating wounds and sores with zinc oxide, the zinc-oxide content must be kept within a narrow range. It is desirable to achieve the effect of Sections 1–3, but not to exceed the limit so that Section 4 occurs.

In principle the skin is made up of two layers, i.e. the upper skin layer (epidermis) and the lower skin (dermis). Epidermis has a thickness of about 100 μm, while the thickness of dermis varies between 3 to 5 mm, depending upon its location in the anatomy. The zinc concentration in epidermis is approximately six times greater than that in dermis (Reference: Molokhia mm. Portnoy B. Neutron activation analysis of trace elements in skin. Br J. Dermatol 1969; 81; 759–762). This is probably why tested ointments of high zinc concentrations are well tolerated when treating superficial skin complaints. The situation is quite different, however, in the case of ulcerated skin, where the skin deficiency also involves dermis. Because this layer of the skin contains far less zinc, the cells of the layer are adapted to such levels. Applications of excessively high dosages of zinc to these sections of the skin is liable to damage the cells instead of stimulating the same. It has been found that the proliferation of human fibroblasts decreases in vitro when the zinc-oxide concentration exceeds 10 μg ZnO/ml=$12\times10^{-5}$M (Reference: Priestley G. C. Brown J. C. Acute toxicity of zinc pyrithione to human skin cells in vitro. Acta Derm Venerial (Stockh.) 1980:60:145–148). Fibroblasts are the cell type which produce collagen in the structuring of connective tissue in damaged dermis.

Since zinc ointments and zinc tape are suitable only for certain kinds of sores, as beforementioned, strenuous efforts have been made to find a suitable method of applying zinc oxide locally to an open sore. In this regard, zinc oxide has been applied to open sores in an absorbent air-permeable bandage, such as a dressing. It has been found difficult, however, to bind the zinc oxide to the dressing in a satisfactory manner, while at the same time, dispensing suitable amounts of zinc oxide from the dressing to the sore.

The problem associated herewith is totally different from that of binding zinc oxide to a tape. Attempts have been made to bind zinc oxide in dressings with the same kind of binder used with zinc tape. The dressings were rendered totally unusable, however, among other things because they created pronounced skin irritation and because they had reduced absorption ability.

Tests have also been carried out with zinc oxide slurried in water, the dressings being saturated with the slurry and then dried. The tests did not show a good result. The zinc oxide did not bind firmly to the dressing material, but quickly departed therefrom in the form of dust. Dressings saturated in zinc oxide suspensions also became very stiff and inflexible, since the suspension remained mostly in the outer layers of the dressing, thereby resulting in an inhomogenous impregnation of the dressing. In order to achieve successful treatment it is imperative that the dressing is pliable and conforming, with good contact with the sore and therewith optimal effect. In addition it is important that zinc is continuously dispensed to the sore in the correct dosages over an extended period of time, so-called slow release dosing.

Unless the zinc oxide is uniformly distributed throughout the dressing, an excessively high concentration of zinc will be applied initially to the surface of the sore, with a subsequent active period of short duration.

A dressing according to the invention containing substance for cleansing sores and stimulating the healing thereof is characterized in that the substance comprises zinc oxide in an amount of 1-10% by weight calculated on the dry weight of the dressing, the zinc oxide being bound in the structure of the dressing blank or preform, adhered in homogenous distribution on the individual fibres by means of a tissue-compatible, preferably water-soluble polymer for so-called slow release dosing when applied to open sores.

The method according to the invention for preparing dressings containing substance for cleansing sores and stimulating the healing thereof is characterized by feeding a web of dressing-blank material through a press nip, preferably a gauze web; transferring to the dressing blank upstream of the roll nip a suspension containing said substance in the form of zinc oxide; causing the zinc-oxide particles to be present into the structure of the dressing blank and bound to the individual fibres of said blank during its passage through the roll nip, the zinc-oxide particles being bound by means of a tissue-compatible, preferably water-soluble polymer present in the suspension; and by drying the dressing-blank web and converting the same to dressings.

The invention will now be described in more detail with reference to the accompanying drawings, in which FIG. 1 illustrates schematically the method of applying zinc oxide to the dressing blank;

FIG. 4 illustrates diagrammatically differences in the healing effect of dressings provided with zinc oxide according to the invention and dressings which lack zinc oxide.

Figure 1:
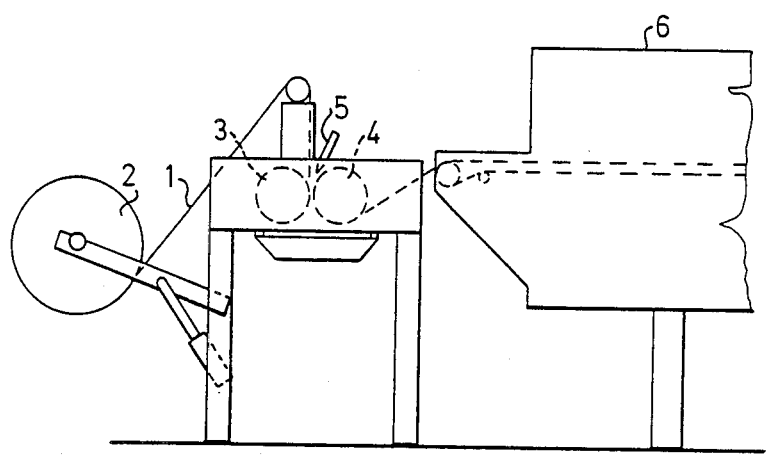

In the apparatus or mill illustrated in FIG. 1 a gauze web 1 is fed continuously from a storage reel 2 through the press nip of a pair of rolls 3,4, to which a zinc-oxide suspension is supplied continuously from a nozzle 5. The press nip is sealed off and the supply of suspension through the nozzle is controlled by a level meter (not shown) in a manner to sustain the requisite amount of suspension above the roll nip.

The suspension is thus dispensed to the gauze web as the web is fed between the rolls 3,4.

As the gauze web passes through the roll nip, the zinc-oxide particles are pressed into the structure of the gauze and adhere to the individual fibres thereof. In addition to zinc oxide the suspension also contains polyvinyl pyrrolidone, this substance being added in order to bind or fix the zinc-oxide particles on the gauze fibres. The gauze web, now saturated with said suspension, is fed from the rolls to a drying oven 6. When dry, the gauze web can be converted to dressings in a conventional manner (not illustrated).

Subsequent to treating the gauze web in the aforedescribed manner, the zinc oxide and polyvinyl pyrrolidone (PVP), for example of the kind retailed under the trade name KOLLIDON®, is found homogenously distributed in the finished dressing and the dressing cannot be distinguished from an untreated dressing.

Figure 2:
FIG. 2 is an enlarged view of a gauze fibre or filament of a dressing according to the invention.
Figure 3:
FIG. 3 is an enlarged view of individual gauze fibres according to FIG. 2.

FIGS. 2 and 3 illustrate fibres to which zinc oxide has been bound in the aforedescribed manner. The reproduced pictures were taken with a scanning electronmicroscope. In the view reproduced in FIG. 2, a gauze fibre has been enlarged 440 times, while FIG. 3 shows individual fibres in FIG. 2 enlarged 2000 times. The homogenous distribution of zinc oxide in the dressing can clearly be seen from FIGS. 2 and 3.

All open sores continuously secrete tissue fluid to a greater or lesser extent. When a dressing according to the invention is placed over an open sore, zinc oxide is released from the dressing to the moist environment and is transferred to the sore at the same rate as secretion from the sore is absorbed by the dressing. The use of PVP provides constant dispensing of zinc oxide from the dressing to the sore over an extended treatment period.

Tests have also been made with other polymers, such as carboxy methyl and the like, polyethylene glycols etc., from which it could be ascertained that polyvinyl pyrrolidone is the most suitable, due to its atoxic and hygroscopic properties. A composition which proved satisfactory from a handling aspect was also produced by varying the amount of polymer used from 0.1 to 5% by weight, calculated on the dry weight of the dressing, and the amount of zinc oxide used from 1 to 10% by weight and even values outside these limits.

The treatment of open sores and like afflictions with zinc dressings according to the invention has been investigated with the purpose of establishing the effect afforded by the dressing, the type of sore with which it can be used, and the most suitable sore treatment technique.

As will be understood from the introduction, the amount of zinc oxide in the finished product is decisive in achieving good treatment results.

A number of introductory tests were carried out during the background work associated with our dressing. An 86 year old woman suffering comprehensively from sores in the lower leg agreed to take part in a first test. The sores had afflicted the woman for 40 years. There was initially used a dressing containing 20% by weight zinc oxide calculated on the weight of the dry dressing. Although the sore was cleansed satisfactorily, the sore increased in size, in other words healing was inhibited. The patient also complained of pain.

In the following series of tests a dressing containing 2% by weight zinc oxide and 1% by weight PVP was used. With this zinc oxide concentration the sore was seen to heal while retaining the cleansing effect. Further pilot tests indicated that the dressing possessed cleansing and healing properties.

Zinc dressings of this lastmentioned composition have been tested with the aid of scientific methodology.

It was surprisingly found that the zinc dressing also had a cleansing effect on necrotic tissue. Necrosis has previously been treated with medicinal preparations containing proteolytic enzymes, for example Varidase ® and Trypure ®, which are intended to be applied directly to a sore, in gel or solution form. The use of proteolytic enzymes, however, is both troublesome and time consuming.

Moreover, treatment with medicinal preparations containing proteolytic enzymes often brings discomfort to the patient. Such preparations may cause pain when applied. Medicines of this kind may also result in skin allergies, especially in the case of long term treatment. Moreover, when carrying out tests on such preparations we have observed local toxic symptoms in some cases.

A further disadvantage with medicinal preparations of the aforesaid kind is that they are suitable only for the treatment of necrosis. The zinc dressing according to the invention have been found to have an extremely good cleansing effect, comparable with that achieved with known medicinal preparations contaning proteolytic enzymes.

This is documented in the following investigation:

With the intention of establishing the cleansing effect of zinc oxide, the dressing according to the invention was compared with an established method of treatment, Varidase ®. Varidase ® was applied to a sore dressing twice a day. The investigation was planned as an open, random study, the result of which was judged by a non-resident, impartial physician.

Of twenty-eight patients suffering from necrotic pressure sores, half were treated with zinc and the other half with Varidase ® over a period of eight weeks. Of the fourteen sores treated with zinc, seven were found to be clean upon completion of the treatment period. The corresponding number of cleansed sores of the batch treated with Varidase ® was six. The conclusion reached from this investigation, which is statistically supported by sequential analysis, is that the two preparations have roughly the same effect when used to treat necrotic sores.

In order to investigate the healing and the cleansing effect of the zinc dressing according to the invention, it was elected to test the dressing on arterial and venous leg sores. Thirty-seven (37) patients were included in this study, these patients being selected at random. Neither the patients themselves nor the nursing staff were aware of the nature of the treatment prescribed. This was made possible by the identical appearance of the different dressing used. The patients were matched in pairs with respect to the type of sores from which they suffered. Of each pair, one patient was treated with a zinc dressing and the other with a dressing containing no zinc oxide (placebo). The dressings of each pair of patients contained the same amount of PVP. A good effect was obtained with 15 of the patients treated with zinc dressing, while eight of the nineteen treated with the placebo dressings improved. After 12 weeks, eleven of the sores treated with zinc were found to have healed completely, and four of the sores treated with the placebo dressings were also found to be healed. Of the sores treated with placebo dressings, six became infected, while of the sores treated with zinc one became infected. (c.f. the Table below).

| Treatment | Good effect of the treatment | Infected during treatment | Number of healed sores after 12 weeks |
|---|---|---|---|
| Zinc (n = 18) | 15 | 1 | 11 |
| Placebo (n = 19) | 8 | 6 | 4 |

The difference in the healing processes between the two treatment groups can be seen from FIG. 4.

The zinc content in serum was also measured in all patients. No patient had serum zinc values above 15 $\mu$mol/l. Since the average age of the patients was 78 years, the result of the serum assays was expected. It could therefore be established that the patients had a zinc deficiency, which is considered a prerequisite for successful zinc therapy, at least in tablet form.

During the tests the sores were washed with common salt solutions prior to applying the dressings. This was done once a day. If the sore seeped excessively, the dressing was changed more than once a day, although one daily dressing sufficed as a rule.

It is known that zinc oxide has an antibacterial effect on *Pseudomonas aeruginosa. Staphylococcus aureus and Streptococcus pyogenes.* In those clinical investigations carried out, puss-coated sores were found to be cleansed and sore infections reduced in all of the cases investigated.

The zinc dressing according to the invention was found to produce a very good result with all of the aforementioned types of sore. No secondary effects were observed, despite the fact that in the case of certain sores, extremely difficult to heal, treatment was continued for four months. Neither were the dressings found to adhere to the sores during treatment, due probably to the water-binding property of PVP.

The zinc dressing according to the invention can therefore be used over a broad spectrum, since it can be applied with good effect both for cleansing necrotic tissue and for healing sores.

The described embodiments do not limit the invention in any way, and several modifications are possible within the scope of the following claims. For example, dispensing of zinc oxide to the sore can be controlled by the amount of zinc allocated to a particular dressing and/or by the polymer selected and its percent by weight ratio in the dressing. The dressing material may also be other than gauze, for example a non-woven material, where the selection of material also governs the dispensing of zinc ions. The dressing may also include one or more further active substances in addition to zinc oxide. Suitable additives in this respect are antiseptic agents, such as iodine, antibiotica, vitamines, amino acids, proteins, pain killing substances, such as XYLOCAIN ®, and vessel-expanding substances such as nitroglycerine, either per se or in combination.

I claim:

1. Air-permeable dressing for cleaning sores and stimulating the healing thereof, comprising a fibrous dressing blank formed from a multiplicity of individual fibers having zinc oxide bound to each one of the individual fibers of said blank throughout the thickness of said blank, in an amount of 1–10% by dry weight of said dressing, said zinc oxide being bound to the individual fibers of said blank by polyvinyl pyrrolidone, said polyvinyl pyrrolidone being present in an amount of 0.1–5.0% by dry weight of said dressing.

2. Dressing according to claim 1, wherein said fibrous dressing blank is gauze.

3. A dressing according to claim 1, characterized in that it incorporates an antiseptic, such as iodine.

4. A dressing according to claim 1, characterized in that it incorporates antibiotics.

5. A dressing according to claim 1, characterized in that it incorporates vitamins.

6. A dressing according to claim 1, characterized in that it incorporates aminoacids.

7. A dressing according to any one of the preceding claims, characterized in that it incorporates proteins.

8. A dressing according to claim 1, characterized in that it incorporates pain killing substance, lidocaine.

9. A dressing according to claim 1, characterized in that it incorporates vessel-expanding agent, such as nitroglycerine.

* * * * *